United States Patent
Janik et al.

(10) Patent No.: US 10,835,732 B2
(45) Date of Patent: Nov. 17, 2020

(54) CONNECTOR UNIT FOR BLOOD TREATMENT MACHINE TO CONNECT SAID BLOOD TREATMENT MACHINE TO AN EXTERNAL CONTAINER AND BLOOD TREATMENT MACHINE COMPRISING SAID CONNECTOR UNIT

(71) Applicant: B. BRAUN AVITUM AG, Melsungen (DE)

(72) Inventors: Waldemar Janik, Melsungen (DE); Jens Duru, Bebra (DE)

(73) Assignee: B. BRAUN AVITUM AG, Melsungen (DE)

( * ) Notice: Subject to any disclaimer, the term of this patent is extended or adjusted under 35 U.S.C. 154(b) by 12 days.

(21) Appl. No.: 16/286,161

(22) Filed: Feb. 26, 2019

(65) Prior Publication Data
US 2019/0262600 A1 Aug. 29, 2019

(30) Foreign Application Priority Data
Feb. 27, 2018 (DE) .................. 10 2018 104 457

(51) Int. Cl.
*A61M 1/16* (2006.01)
*A61M 39/10* (2006.01)
*A61M 1/14* (2006.01)

(52) U.S. Cl.
CPC .............. *A61M 39/10* (2013.01); *A61M 1/14* (2013.01); *A61M 1/1668* (2014.02);
(Continued)

(58) Field of Classification Search
None
See application file for complete search history.

(56) References Cited

U.S. PATENT DOCUMENTS

| 5,540,265 A | * | 7/1996 | Polaschegg ......... A61M 1/1666 |
| | | | 141/301 |
| 2012/0068455 A1 | | 3/2012 | Gastauer et al. |

(Continued)

FOREIGN PATENT DOCUMENTS

| CN | 201921175 U | 8/2011 |
| DE | 102012002497 A1 | 8/2013 |

(Continued)

OTHER PUBLICATIONS

Fresenius, "5008 Hemodialysis System Operating Instructions", Sep. 2006 (Year: 2006).*

(Continued)

*Primary Examiner* — Bradley R Spies

(57) ABSTRACT

A connector unit for a blood treatment machine connects the blood treatment machine to an external container. The connector unit includes a machine-side line which is designed for being fluid-connected to the blood treatment machine, a container-side line which is designed for being fluid-connected to the container, and an attachment tightly connected to the machine-side line and to the container-side line which is designed for being detachably mounted on a connecting nozzle of the external container so as to fluid-connect the external container to the blood treatment machine. The connector unit can be included on a blood treatment machine.

15 Claims, 5 Drawing Sheets

(52) U.S. Cl.
CPC .............. *A61M 2039/1077* (2013.01); *A61M 2039/1094* (2013.01); *A61M 2205/6036* (2013.01); *A61M 2205/6045* (2013.01)

(56) References Cited

U.S. PATENT DOCUMENTS

| | | |
|---|---|---|
| 2013/0206248 A1 | 8/2013 | Brehm |
| 2013/0245531 A1 | 9/2013 | Brandl et al. |
| 2015/0198278 A1* | 7/2015 | Clements .............. F16L 19/025 |
| | | 285/93 |
| 2016/0213831 A1 | 7/2016 | Brehm |
| 2017/0021079 A1 | 1/2017 | Lura et al. |
| 2017/0120032 A1* | 5/2017 | Miyazaki .............. A61M 39/10 |

FOREIGN PATENT DOCUMENTS

| | | |
|---|---|---|
| EP | 1625867 B1 | 2/2006 |
| EP | 2730304 A2 | 5/2014 |
| JP | 2010184110 A | 8/2010 |
| WO | 2013117340 A1 | 8/2013 |

OTHER PUBLICATIONS

Cajes, W., "Setting up a Haemodialysis Machine Fresenius 5008", Oct. 23, 2015; https://www.youtube.com/watch?v=6DM-3vOjYd4, one page.

German Search Report for German Application No. 10 2018 104 457.7, dated Apr. 18, 2019, with translation, 17 pages.

Extended European Search Report for European Application No. 19 159 385.4, dated Jul. 18, 2019, with translation, 11 pages.

\* cited by examiner

CONNECTOR UNIT FOR BLOOD TREATMENT MACHINE TO CONNECT SAID BLOOD TREATMENT MACHINE TO AN EXTERNAL CONTAINER AND BLOOD TREATMENT MACHINE COMPRISING SAID CONNECTOR UNIT

RELATED APPLICATION

This application claims the benefit of priority of German Application No. 10 2018 104 457.7, filed Feb. 27, 2018, the content of which is incorporated by reference herein in its entirety.

FIELD

The present disclosure relates to a connector unit for a blood treatment machine to connect said blood treatment machine to an external container, a system comprising said connector unit and an external container as well as a blood treatment machine comprising at least one said connector unit.

BACKGROUND

For blood treatment, especially when carrying out a dialysis treatment, it is necessary to prepare an electrolyte solution, i.e. the so-called dialysis fluid. In the dialyser said dialysis fluid flushes the blood of a patient and absorbs small-molecular and medium-molecular substances from the blood.

For preparing the dialysis fluid a blood treatment machine and, resp., a dialysis machine requires purified water (permeate), an acid concentrate and sodium hydrogen carbonate which is contained either in solid form in a cartridge or in liquid form in a canister being connected to the blood treatment machine.

In order to make the substances required for preparing the dialysis fluid available to the blood treatment machine, for example commercially available canisters containing acid concentrates or basic concentrates and, resp., solutions can be placed on the machine bottom of the blood treatment machine and can be connected to the machine via connecting lines.

Alternatively, it is possible to pass said concentrates from a central source directly into the machine.

Usually the required concentrates are provided in canisters, however. Said canisters are usually closed by a conventional lid.

In order to make the concentrates available to the blood treatment machine, the lid of each canister is screwed off and a round threaded adapter which is substantially configured like a conventional canister lid having a round opening for inserting a connecting line is screwed onto the canister. Then the connecting line of the blood treatment machine can be inserted into the canister through the opening within the threaded adapter so that the machine can suck concentrate from the canister via the connecting line.

Said procedure in practice has several drawbacks, however.

Firstly, the separate threaded adapters have to be separately stored even when the blood treatment machine does not require the same for preparing dialysis fluid so that the space required by the entire blood treatment system will increase.

In addition, the separate adapters can get lost during storage and then are not available in the case of need.

Furthermore, the risk of incorrect connections is quite high with this conventional procedure, as the threaded adapters used mostly have the same insertion opening and, in this way, e.g. the connecting line for the acid concentrate may erroneously also be inserted into the canister containing the basic solution.

In conventional dialysis machines or blood treatment machines said error is not detected before the machine has already sucked the wrong concentrate, which endangers the patient's safety.

From the state of the art, various subassemblies for connecting concentrate containers to a blood treatment machine are known.

For example, JP 2010 184 110 A discloses a suspension device for a liquid suction line which includes a cap and a supporting portion for the cap.

Furthermore, EP 2 730 304 B1 discloses a connector for disposable containers to be used in dialysis machines which comprises an external thread adapted to be screwed into a connector of a bag containing pre-mixed dialysis fluid.

In addition, the document WO 2013/117340 A1 discloses a connector for a container including a spiking solution for individually adapting dialysis solutions and concentrations.

Moreover, the document CN 2019/21175 U discloses a cover which can be screwed onto a connecting piece of a canister by means of threaded engagement.

A further state of the art is the document EP1625867 B1 which discloses a device for gas supply at two different pressures.

SUMMARY

In view of the state of the art, the object underlying the present disclosure is to provide a connector unit for a blood treatment machine for connecting the blood treatment machine to an external container which reduces the number of single parts required and thus facilitates manipulation.

A connector unit for a blood treatment machine to connect the blood treatment machine to an external container according to the disclosure includes:
- a machine-side line which is designed for being fluid-connected to the blood treatment machine,
- a container-side line which is designed for being fluid-connected to the container, and
- an attachment tightly and, resp., permanently connected to the machine-side line and the container-side line which is designed for being detachably mounted to a connecting piece/connecting nozzle of the external container so as to fluid-connect the external container to the blood treatment machine.

Hence, the core of the disclosure consists in connecting the threaded attachment/adapter for the concentrate canister separately configured according to prior art tightly, preferably in accordance with non-detachably/non-removably, to the connecting line of the blood treatment machine and, resp., integrating in the latter to form a subassembly. Said integration of the threaded adapter with the connecting line of the dialysis machine can safeguard that the adapter neither has to be separately supported nor can get lost, but is an integral/permanent part of the blood treatment system, especially of the connector unit of the blood treatment machine. This helps to improve the handling of the connecting line as compared to prior art. Moreover, the space required by the blood treatment system as well as the number of the required single parts can be reduced. Finally, it is possible to prevent incorrect connection of a wrong concentrate to a wrong connector of the blood treatment machine, as each attachment is invariably associated with a particular connecting line and therefore, at the same time, association of the connecting line with a particular external container is obtained/ensured.

According to a preferred aspect of the disclosure, the attachment of the connector unit is further configured so that it can be exclusively mounted to a connecting piece of an external container of a particular type, wherein the type of external container corresponds to the content of the container (e.g. the container is of the "acid concentrate container" type or "basic concentrate container" type etc.), which ensures that exclusively the external container of one particular desired type corresponding to the content of the container can be fluid-connected to the blood treatment machine by means of the connector unit.

In other words, a particular attachment can be connected for example only to an acid container or else only to a base container. The particular attachment thus can be connected only to each container of the acid container type or only to each container of the base container type.

It is required in this case that the individual containers of each type are configured to be uniform at least with respect to their connecting piece. It is further taken as a basis that the connecting pieces of a container including acid and a container including base are different from each other. The type of container accordingly denotes the "acid container" type or "base container" type etc. The type of external container thus corresponds to the content of the container and determines the configuration of the connecting piece of the external container which serves as mounting piece for the attachment of a connector unit of a blood treatment machine.

Such unambiguous association of an attachment of a connector unit according to the lock-and-key principle with a special type of external container corresponding to a defined content of the container may prevent a container including acid from being erroneously connected to a connector which in fact should be connected to a container including base. An attachment provided for an acid container cannot be mounted to a base container due to its geometric configuration. This helps to significantly increase the patients' safety.

In accordance with an aspect of the disclosure, the attachment of the connector unit is further designed for being held by form locking or frictional locking to the connecting piece of the external container of a predetermined type when the attachment is mounted on the connecting piece.

Concretely speaking, the attachment may be, for example, in the form of a shape-elastic bellow and, resp., of a rubber bellow which can be slipped and, resp., drawn over the connecting piece of the external container.

Said shape-elastic attachment of the connector unit may have a substantially elastically deformable cylindrical base member the diameter of which is smaller in the idle state than the diameter of the connector piece of the external container and which therefore can be applied to the connecting piece of the external container in a stretched condition only.

Alternatively, the frictional connection can as well be realized in that the attachment is in the form of a dimensionally stable cap which has a preferably smooth inner face and can be attached substantially free from play to a corresponding connecting piece of the container having a smooth outer face of the connecting piece, with frictional connection between the inside of the cap-shaped attachment and the outside of the connecting piece of the external container holding the attachment on the container.

According to another aspect of the disclosure, the attachment can also be configured to be rotatable about the container-side line and as a dimensionally stable cap, with the dimensionally stable cap preferably having a female thread which is designed to be engaged in a matching male thread of the connecting piece of the external container of the predetermined type. The attachment then is positively held on the connecting piece of the external container.

Alternatively, also other types of form locking are imaginable such as e.g. a bayonet closure, an anchoring by means of locking arms engaging in recesses or via undercut. The form locking offers the advantage of an especially safe and stable anchoring of the attachment of the connector unit to the connecting piece of the external container.

In accordance with another aspect of the disclosure, the connector unit in addition includes a reinforcing element which in the area of the attachment and beyond the area of the attachment extends toward a container-side end of the container-side line of the connector unit for a defined length portion along the container-side line.

In other words, the reinforcing element helps to reinforce the container-side line in the area of the attachment and somewhat beyond the latter. Said reinforcement facilitates handling of the connector unit as well as the mounting of the connector unit by means of the attachment to an external container, as the container-side line will not randomly buckle.

According to another aspect of the disclosure, at the container-side line and/or at the reinforcing element, preferably adjacent to the attachment, at least one limiting element is provided which limits an axial movement of the attachment along the longitudinal axis of the container-side line and/or of the reinforcing element.

If a reinforcing element is provided, the at least one limiting element is preferably arranged on the reinforcing element. Unless a reinforcing element is provided, the at least one limiting element is provided at the container-side line.

The limiting element preferably takes the shape of a projection and, resp., of a shoulder or else of an annular peripheral projection on which the attachment rests, thus preventing shifting along the longitudinal axis of the reinforcing element.

Concretely speaking, the limiting element may also be in the form of a rubber ring which is pushed onto the reinforcing element. Of preference, the attachment is so-to-speak prevented from axially moving in both directions on the one side by the at least one limiting element and on the other side by a grip member of the connector unit.

According to another aspect of the disclosure, the connector unit further includes at least one sealing element which is arranged on the reinforcing element and/or the machine-side line and which is designed for fluidically sealing a clearance between the outside of the reinforcing element and, resp., the machine-side line and an inside of a connector of the blood treatment machine, when the reinforcing element and, resp., the container-side line is inserted in the connector/a holding fixture of the blood treatment machine. In other words, at least one, preferably two, sealing element(s) is/are provided which is/are disposed at the connecting nipple preferably in the area of the reinforcement and which is/are designed for fluidically sealing a clearance between the outside of the connecting nipple, preferably of the reinforcement, and an inside of the holding fixture of the blood treatment machine and/or of the connecting nozzle of the external container, when the reinforcing element is inserted in the connector of the blood treatment machine or the connecting nozzle of the container.

In practice, the container-side line and, resp., the reinforcing element is inserted into and, resp., stored in the connector/holding fixture of the blood treatment machine during a rinsing operation or for storage, when the connecting line is not required.

According to another aspect of the disclosure, the connector unit further comprises a release device which releases fluid flow between the connector unit and the external container only when the attachment of the connector unit is correctly mounted at a predetermined mounting position on the connecting piece of the external container. The fluid flow is preferably released by the release device only when the connector unit is correctly attached to the blood treatment machine (for example during disinfection or a rinsing operation). Otherwise, for example during hot disinfection, hot disinfectant could flow out of the machine, thus increasing the risk of injury for a user.

The release device can be configured solely by the connector unit or jointly by the connector unit and the external container.

Concretely speaking, the release device may be a reed contact, for example, in which the attachment is equipped with a reed contact and the connecting piece of the external container is equipped with a magnet. Only when the contact is closed by the vicinity of the magnet, can the connector unit open a respective valve and release supply of the concentrate to the blood treatment machine.

Furthermore, in the connector unit, too, a capacitive sensor may be incorporated which reacts to an appropriate material of the external container and thus determines whether the attachment of the connector unit has correctly been mounted on the connecting piece of the container.

Alternatively or additionally, also the use of a reflecting light barrier is imaginable which determines that the connecting piece of the container is correctly inserted in the attachment of the connecting line and only in that case releases fluid flow between the connector unit, the container and the blood treatment machine.

This helps to prevent the external containers from being left open, which bears the risk of potential contamination by particles penetrating from the ambient air, which ensures concentrate being sucked via the container-side line only when the connector unit is tightly connected to the external container.

Another aspect of the present disclosure relates to a blood treatment machine comprising a connector unit according to the disclosure which is fluid-connected to a predetermined connector of the blood treatment machine via the machine-side line of the connector unit.

Preferably, the connector unit is permanently coupled to the blood treatment machine via the machine-side line of the connector unit. Said fixed connection between the connector unit and the blood treatment machine and the exclusive connectability between the attachment of the connector unit and only the external container which includes the correct concentrate (acid or base) allows to safeguard that the blood treatment machine can suck only the correct concentrate via each connector. This helps to increase the safety when preparing dialysis fluid.

A further aspect of the disclosure relates to a blood treatment machine comprising a plurality of connector units in accordance with the present disclosure each of which is fluid-connected to a respective dedicated and predetermined connector of the blood treatment machine. Each attachment of each connector unit of the plurality of connector units is configured such that the attachment can be detachably mounted only to the connecting piece of an external container of a respective predetermined type (for example acid container or base container), the type of container corresponding to the content of the container.

In other words, the blood treatment machine thus includes, for example, a connector unit for supplying acid concentrate which comprises an attachment adapted to be mounted only to containers including acid concentrate and a connector unit for supplying basic concentrate which comprises an attachment adapted to be mounted only to a container including base concentrate.

It is further also advantageous that, according to another aspect of the disclosure, at least one but preferably each of the connector units of the blood treatment machine additionally includes a release device which releases fluid flow between the blood treatment machine and the respective dedicated external container only when the attachment of the respective connector unit is correctly mounted at a predetermined mounting position on the connecting piece of the respective external container.

In other words, another safety level is introduced by the release device to ensure that for fluid exchange between the blood treatment machine and the external container not only the respective correct type of external container (acid container or base container) is connected to the respective correct connector unit via the attachment, but that the fluid flow is released only when the attachment is in fact mounted correctly and tightly to the respective external container.

In this way, a container cannot happen, with its attachment of the connector unit being only loosely attached to the connecting piece of the container, to be left for a quite long period of time while the blood treatment machine prepares dialysis fluid, without this is noticed by the staff members.

Rather, it is indicated to a user immediately when the connector unit is mounted to the connecting piece of the external container that the attachment is not correctly mounted on the connecting piece of the external container. In this way, contaminations of the concentrates and, resp., of the content of the containers are avoided, as containers are prevented from being exposed to the ambient air over quite long time while being in a just loosely closed condition.

Another aspect of the disclosure further relates to a system consisting of a connector unit according to the present disclosure and an external container, the system preferably having a release device which releases fluid flow between the connector unit and the external container only when the attachment of the connector unit is correctly mounted at a predetermined mounting position on the connecting piece of the external container.

Already existing blood treatment machines may be retrofitted with such system.

BRIEF DESCRIPTION OF THE DRAWING FIGURES

Further advantages and features of the present disclosure will be evident from the following description of preferred embodiments with reference to the related figures, wherein:

FIG. 1 shows a connector unit for a blood treatment machine for connecting the blood treatment machine to an external container, FIG. 2a shows a connector unit for a blood treatment machine for connecting the blood treatment machine to an external container in a position during a rinsing operation of the blood treatment machine in which the container-side line and the reinforcing element are inserted in a holding fixture/ connector of the blood treatment machine;

DETAILED DESCRIPTION

Figure 1:
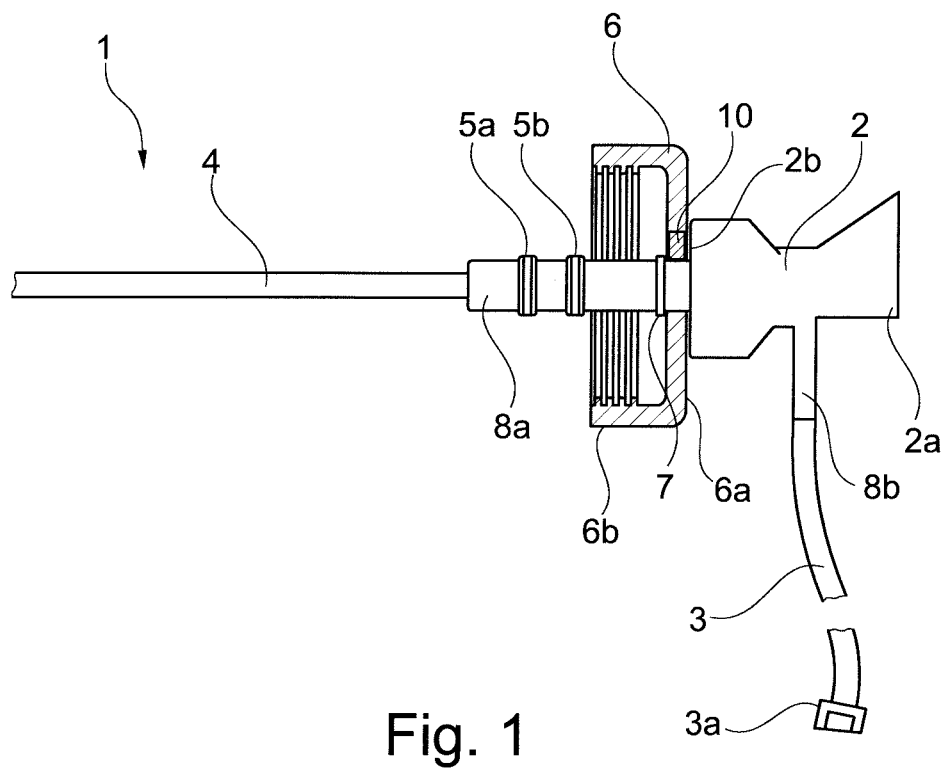

FIG. 1 illustrates a connector unit 1 for a blood treatment machine for connecting the blood treatment machine to an external container (not shown in FIG. 1) comprising a machine-side line (connecting line) 3 which is designed for being fluid-connected to the blood treatment machine, a container-side line (suction line/suction tube) 4 which is designed for being fluid-connected to the external container and, resp., to be inserted into a container, and an attachment 6 fixedly connected to the machine-side line 3 and the container-side line 4 which attachment is designed for being detachably mounted to (screwed onto/into or slipped onto/inserted into) a connecting piece/connecting nozzle of the external container so as to fluid-connect the external container to the blood treatment machine.

For better handling, the connector unit 1 includes a type of plug/grip member 2 in the form of an L piece preferably made from rigid (plastic) material on/at which further a grip 2a is formed by which a user can manipulate the connector unit/plug 2 and which is preferably ergonomically adapted to a user's hand. The plug 2 has two connecting nipples 8a, 8b fluid-connected to each other which are substantially aligned perpendicular with each other and to which the machine-side (connecting) line 3 and the container-side (suction) line 4 are attached in a fluid-tight manner. Alternatively, the lines 3, 4 may as well be inserted in the connecting nipples 8a 8b and, resp., in the plug 2.

Although, in the present exemplary embodiment, the two connecting nipples 8a, 8b of the plug fluid-connected to each other are arranged perpendicular with each other, the present disclosure is not limited to said angle, however, and the two connecting nipples 8a, 8b may as well be arranged at any other angle with each other.

In addition, each of the connecting nipples 8a, 8b may also be fixedly connected to the lines 3 and 4 instead of being connected to the lines 3 and 4 via a plug-type connection (by inserting or attaching).

Finally, the plug 2 forms, on its side facing the container, a stop preferably in the form of a collar 2b which projects radially from the container-side connecting nipple 8a in ring shape. Especially the container-side connecting nipple 8a preferably includes at its proximal end portion a type of reinforcement, i.e. the outer diameter thereof at its proximal end portion is somewhat larger than at its distal end portion.

The lines 3, 4 are rigid or flexible lines. The machine-side line 3 is preferably permanently fluid-connected to the blood treatment machine. However, it is also alternatively possible to provide the machine-side line 3 at its end facing the blood treatment machine with a connecting piece/coupling 3a which is preferably connectable to a coupling specifically formed for this purpose at the blood treatment machine.

The container-side line 4 is inserted or insertible in an opening of the external container/canister and preferably is in direct contact with the concentrate contained in the external container/canister.

The length of each of the lines 3, 4 may be variable, offering the advantage of sucking concentrates provided in external containers which deviate from the common canister geometry/size or container geometry/size, respectively. For example, also canisters that are higher than common canisters can be emptied without any residual concentrate remaining in the canister.

In the present embodiment, the attachment 6 is in the form of a cap-shaped dimensionally stable component including a cap bottom 6a configured to have a central through bore and a peripheral wall 6b forming a female thread, which component is designed for engaging in a male thread of a connecting piece/connecting nozzle of the external container.

The through bore within the cap bottom 6a of the attachment 6 substantially has an inner diameter which allows the container-side connecting nipple 8a of the plug 2 to be inserted. Alternatively, it is also possible, however, to form the plug 2 and the attachment 6 in one (material) piece. The container-side connecting nipple 8a further is dimensioned so that it extends along the container-side line 4 in the area of the attachment 6 and there beyond for a defined length toward the container-side end of the container-side line 4 (not shown).

In the present embodiment, the connecting nipple 8a substantially takes the shape of a tube to which the container-side line 4 is attached so as to provide a fluid passage to the machine-side line 3.

Furthermore, the connector unit 1 according to the present embodiment includes a limiting element 7 preferably in the form of a ring-type shaft locking clip which is provided at the connecting nipple 8a preferably in the area of the reinforcement thereof and, in this embodiment, is configured as a rubber ring peripheral around the connecting nipple 8a and being pushed onto the connecting nipple 8a. Alternatively and/or additionally, also radial projections may be provided at the connecting nipple 8a, however, which adopt the function of the limiting element.

As illustrated in FIG. 1, the limiting element 7 is arranged in direct vicinity of the cap-shaped attachment 6, especially of the cap bottom 6a thereof, viz. on the side of the attachment 6 and, resp., of the cap bottom 6a facing the container-side end of the connecting nipple 8a. In other words, the attachment 6 and, resp., the cap bottom 6a thereof thus is/are clamped between the limiting element 7 and the stop 2b and thus are fixed in the axial direction.

As is moreover evident from FIG. 1, the connector unit 1 further includes at the connecting nipple 8a, preferably in the area of the reinforcement thereof, two sealing elements (rubber rings) 5a and 5b which are arranged to be spaced apart from each other in the axial direction of the connecting nipple 8a at/on the latter and, in this way, form a type of double seal. In the event that the container-side line 4 is slipped/pulled over the connecting nipple 8a, the two sealing elements 5a, 5b are dimensioned so that they extend radially over the outer radius of the slipped-on line 4.

In the present embodiment, the sealing elements 5a and 5b are configured as sealing rings. There may be any number of sealing elements, but at least one sealing element must be present. The sealing elements 5a and 5b are fixed in position along the connecting nipple 8a by the fact that each of them is embedded between two projections (shaft rings) which are annularly peripheral around the connecting nipple 8a so that they cannot move away from their predetermined position in the axial direction of the connecting nipple 8a.

In addition, the connector unit 1 comprises a release device 10 (shown only implicitly in FIG. 1) which ensures that the fluid exchange between the blood treatment machine and the external container via the connector unit 1 takes place only when the attachment 6 of the connector unit 1 is correctly (and completely) mounted on the connecting piece of the external container.

FIG. 2 illustrates the connector unit 1 according to the disclosure from FIG. 1 which forms a rinsing bridge with the blood treatment machine during a rinsing operation of the latter.

Concretely speaking, the container-side line 4 and the connecting nipple 8a are inserted/plugged into an appropriately shaped receiving aperture 20 of the blood treatment machine 21. The connecting nipple 8a in this condition is inserted into the receiving aperture 20 of the blood treatment machine 21 only partially up to the point at which the attachment 6 comes to lie on the surface of the blood treatment machine 21, thus preventing the connecting nipple 8a from being further inserted into the receiving aperture 20 of the blood treatment machine 21.

Figure 2A:
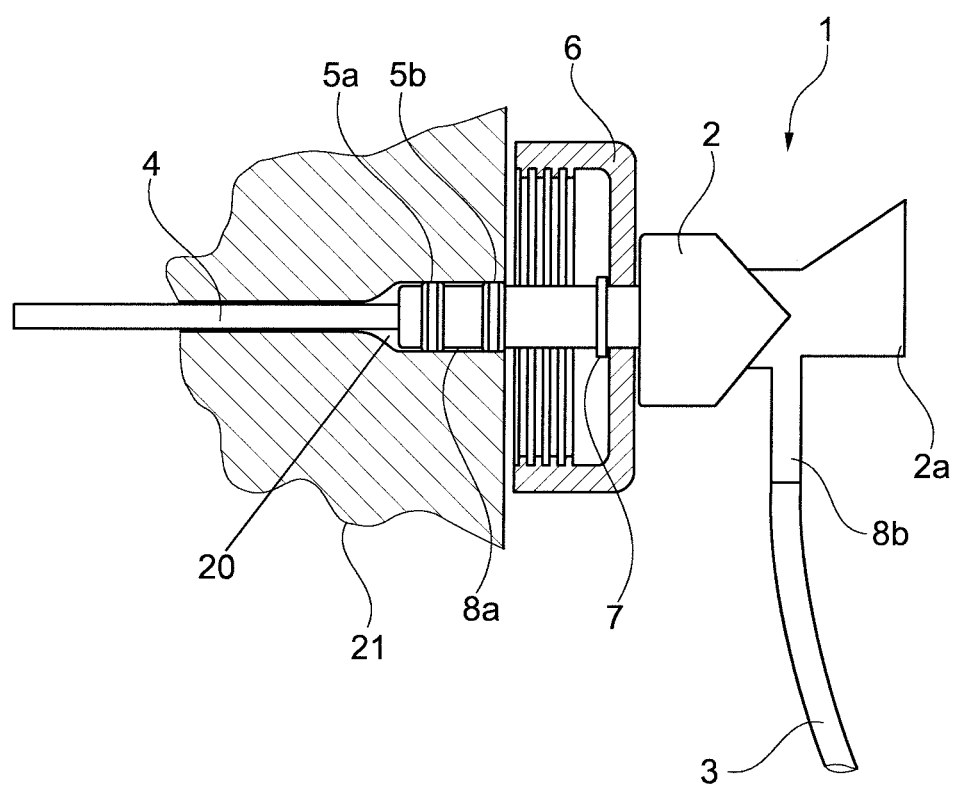
FIG. 2b shows a variant of the arrangement from FIG. 2a in which the blood treatment machine has a connecting piece including a male thread.

As is illustrated in FIG. 2a, in this condition the sealing elements 5a and 5b fluidically seal the clearance between the outside of the connecting nipple 8a and an inside of the receiving aperture 20 of the blood treatment machine 21 in the reinforcing area of the connecting nipple 8a, thus preventing fluid, such as rinsing fluid, from inadvertently leaking from the receiving aperture 20 of the blood treatment machine 21 to the outside.

The position shown in FIG. 2 is the preferred position of the connector unit 1, when the latter is not required or must be located within the blood treatment machine within the scope of a machine-side rinsing operation or, resp., disinfection.

In said position, as illustrated in FIG. 2a, the attachment 6 rests on the outer machine surface. At the same time, the sealing elements 5a, 5b seal the clearance between the connecting nipple 8a and the blood treatment machine 21 so that no fluid is allowed to flow past the sealing elements 5a, 5b out of the machine 21 to the outside. This makes sure that also the machine-side line 4 can be rinsed and, resp., disinfected during the rinsing operation of the blood treatment machine 21.

This is extremely important as an external disinfection of the components of the attachment 6 of the limiting element 7 and of the plug 2 is not provided so that the sealing elements 5a and 5b are also indispensable for preventing possible particles passing from outside through the rinsing seat into the rinsing fluid and thus from being circulated in the entire blood treatment machine 21.

Alternatively or additionally, it is possible for the connector unit 1 to be fastened/screwed in this position via the attachment 6 to the blood treatment machine 21 during the rinsing operation of the blood treatment machine 21.

Figure 2B:
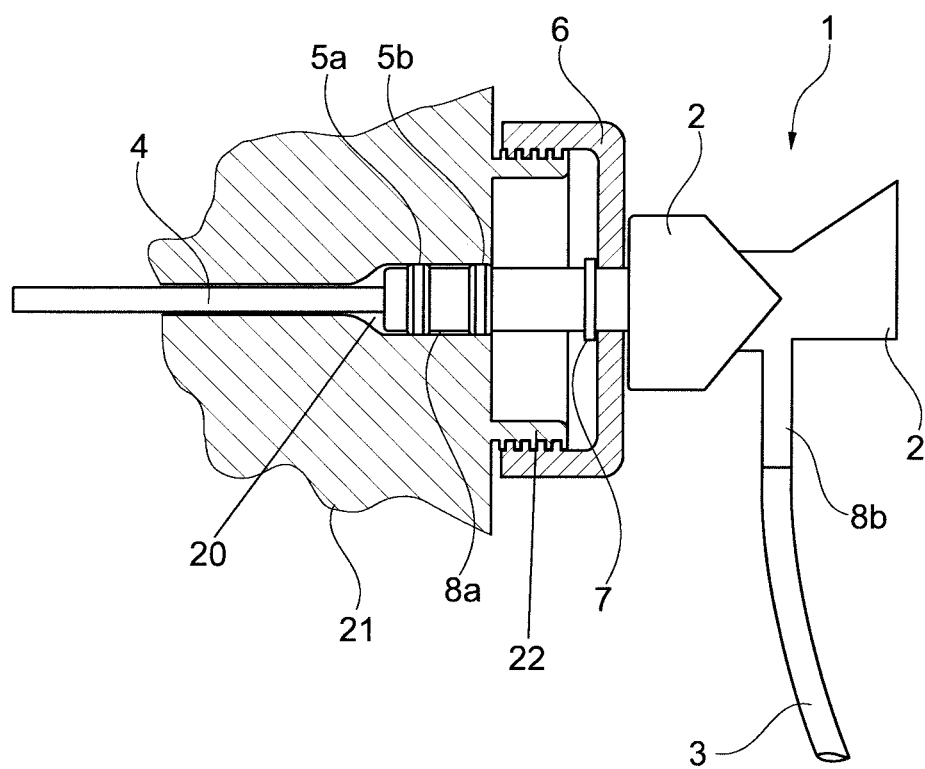

In said embodiment shown in FIG. 2b, the machine surface includes an appropriate connecting piece 22 onto which the attachment 6 is screwed. The connecting piece of the blood treatment machine 21 thus must exhibit a male thread.

In this variant, the sealing elements 5a and 5b would not be absolutely necessary, as by the threaded engagement of the connecting piece of the blood treatment machine and of the attachment 6 the connector unit 1 is safely retained on the blood treatment machine 21 and, in addition, the circulation of the rinsing fluid would be safely shielded against external contaminants.

This embodiment would allow for also disinfecting and, resp., rinsing even the inside of the attachment 6 and the limiting element 7 during automatic machine-side disinfection and, resp., a rinsing operation. In said embodiment, the sealing elements are configured to be not completely sealing or at least one additional opening is provided in the surface of the blood treatment machine 21 inside the connecting piece to feed rinsing fluid into the interior of the attachment 6.

Figure 3:
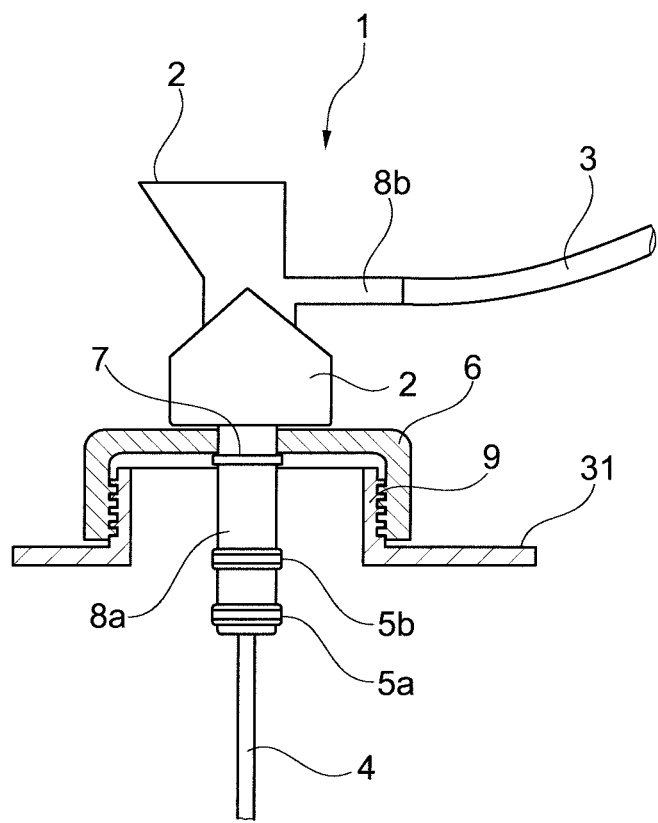
FIG. 3 shows a connector unit for a blood treatment machine for connecting the blood treatment machine to an external container according to the disclosure which is mounted on the external container at a correct mounting position.

FIG. 3 illustrates the connector unit according to the disclosure of FIGS. 1 and 2 in a position in which the connecting line is positively connected to an external container matching the attachment 6 and, resp., to the connecting piece 9 thereof.

The external container includes, as afore-illustrated, a connecting piece 9 having a male thread which is engaged in the female thread of the attachment 6.

In this embodiment, the attachment 6 is pivoted about the proximal reinforcing portion of the connecting nipple 8a and the container-side line 4 so that, when the connector unit 1 is mounted to the container 31, the connecting nipple 8a and the container-side line 4 can be easily inserted into the container 31 and then the attachment 6 can be screwed onto the connecting piece 9 without the machine-side line 3 connected to the blood treatment machine 21 being twisted.

If, alternatively, the attachment 6 is in the form of a shape-elastic (rubber) bellow, the attachment 6 is simply slipped over the male thread and, resp., the connecting nozzle (connecting piece) 9 of the container 31. Advantageously, said attachment 6 is made from acid-proof shape-elastic material such as silicone. In general, it is advantageous when the components of the connector unit 1, especially the attachment 6, are made from plastic material.

The disclosure provides for adjusting the diameter of the attachment 6 depending on the type of container to the connecting piece of which the attachment 6 is to be connected. In order to avoid, for example, an incorrect connection between the connectors for acid concentrate and basic concentrate and the containers for acid concentrate and basic concentrate, the diameter of the attachment 6 provided for connection to the container for the acid concentrate can be adjusted to be larger or smaller than the diameter of the attachment of a different connector unit which is provided for being connected to a container for basic concentrate.

This requires the corresponding male threads of the respective dedicated containers including acid concentrate and, resp., basic concentrate equally having a different diameter analogously to the configuration of the attachment 6 so that the respective attachment and the respective dedicated type of container can be connected exclusively to each other according to the lock-and-key principle.

In addition to that, color coding of the attachment 6 or of any other component of the connector unit and, resp., of the respective dedicated type of container is possible.

For example, acid concentrates can always be stored in red containers to each of which only an attachment colored in red can be screwed. This will further facilitate correct mounting of the correct attachment to the respective dedicated container for a user.

It is moreover imaginable to differently design the thread direction so that, for example, for connecting the adapter 6 to the dedicated container for acid concentrate a right-hand thread or, resp., left-hand thread is used and for connecting a dedicated other attachment 6 to a container for basic concentrate the respective other one of the left-hand and right-hand threads is used. Thus, incorrect mounting of an attachment to a type of container which is not provided would equally be excluded.

Since open concentrate canisters bear the risk of potential contamination by particles possibly penetrating from outside into the container, the connector unit 1 and, resp., the attachment 6 may be provided to be equipped with a release device 10 as already briefly mentioned at the beginning of this description, in order to safeguard that a concentrate is sucked via the connector unit 1 through the blood treatment machine only when the connector unit 1 is tightly connected to the container.

For instance, the threaded attachment 6 may be equipped with a reed contact and a dedicated type of container may be equipped with a magnet. Only when the contact is closed by the vicinity of the magnet, would the release device 10 release fluid flow between the blood treatment machine 21 and the container 31 by opening an appropriate valve e.g. inside the plug 2 or the container 31 or the blood treatment machine 21, thus enabling the appropriate concentrate to be supplied from the container.

Furthermore, a possible release device 10 would also be a capacitive sensor or a reflection light barrier which indicates the correct mounting of the container 31 to the connector unit 1 by using a transmitter and a receiver within the connector unit 1.

Figure 4:
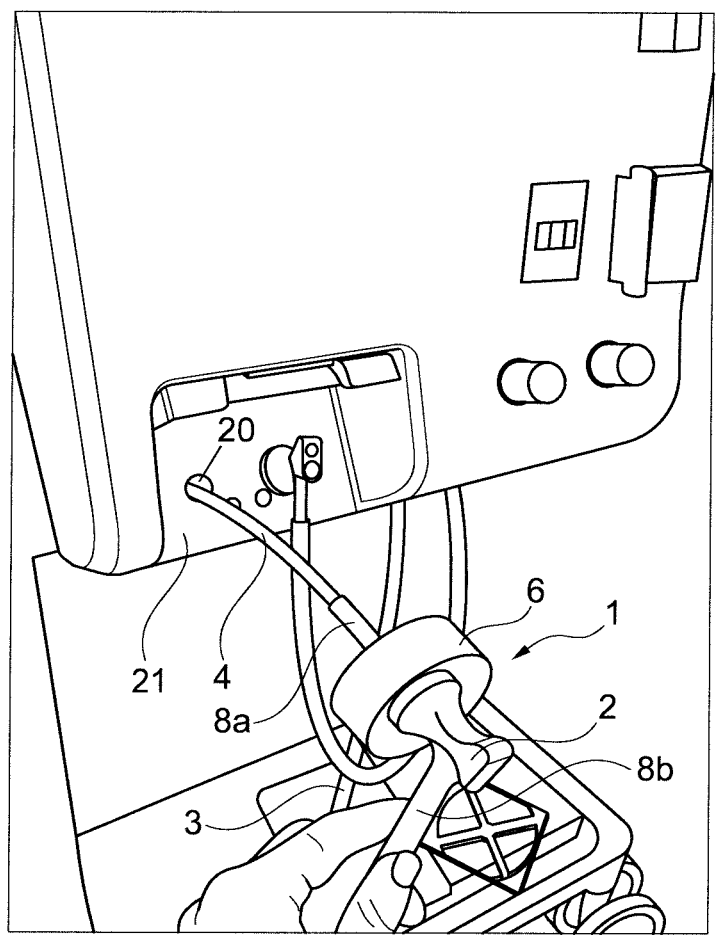
FIG. 4 shows a blood treatment machine comprising a connector unit according to the disclosure.

FIG. 4 illustrates a blood treatment machine 21, in the present case a dialysis machine, which is equipped with a connector unit 1 according to the disclosure. The connector unit 1 according to the disclosure is arranged on the blood treatment machine 21 via the machine-side line 3 of the connector unit 1 in this case.

For a rinsing operation the connector unit 1 may be arranged on the blood treatment machine 21 by inserting at least also the container-side line 4 and, where necessary, also the reinforcing element 8 into a corresponding holding fixture of the blood treatment machine 21.

The connector unit 1 and, consequently, also the attachment 6 dedicated to the connector unit 1 is permanently fixedly associated with the blood treatment machine 21. Therefore, no separate attachment which has to be separately stored and may get lost is provided. Thus, the structure of the blood treatment system is facilitated.

The invention claimed is:

1. A connector unit for a blood treatment machine comprising:
   a machine-side line that fluidly connects to the blood treatment machine,
   a container-side line that fluidly connects to a connecting nozzle of an external container in a treatment configuration and fluidly connects to a receiving aperture of the blood treatment machine in a disinfecting configuration,
   a plug-type connecting piece defining a fluid passage therethrough between the machine-side line and the container-side line, and
   an attachment permanently supported by the plug-type connecting piece, wherein the attachment is sized and shaped to fluidically seal and detachably couple with the connecting nozzle of the external container in the treatment configuration, and with the receiving aperture of the blood treatment machine in the disinfecting configuration.

2. The connector unit according to claim 1, wherein the attachment is provided as a coding unit, which is dimensioned or shaped individually, so that the attachment is mountable exclusively onto the connecting nozzle of the external container which is of a predetermined type corresponding to a content of the container.

3. The connector unit according to claim 1, wherein the attachment is designed for being retained, by form locking or frictional locking, on the connecting nozzle of the external container when the attachment is mounted on the connecting nozzle.

4. The connector unit according to claim 1, wherein the attachment is a shape-elastic bellow which is slipped over the connecting nozzle of the external container.

5. The connector unit according to claim 1, wherein the attachment is configured to be rotatable about the container-side line and to be a dimensionally stable cap having a female thread which is designed to be engaged in a corresponding male thread of the connecting nozzle of the external container.

6. The connector unit according claim 1, comprising at least one container-side connecting nipple connected to the container side line, wherein the connecting nipple, along its length, has a reinforcement which extends from a proximal portion in an area of the attachment, in a distal direction along the container-side line for a defined length, beyond the area of the attachment.

7. The connector unit according to claim 6, further comprising a limiting element near the reinforcement and distally adjacent to the attachment, wherein the limiting element inhibits an axial movement of the attachment relative to a longitudinal axis of the connecting nipple.

8. The connector unit according to claim 6, further comprising at least one sealing element which is disposed on the connecting nipple and which is designed for fluidically sealing a clearance between an outside of the connecting nipple and an inside of at least one of the receiving aperture of the blood treatment machine and the connecting nozzle of the external container.

9. The connector unit according to claim 1, comprising a release device for releasing fluid flow between the connector unit and the external container only when the attachment of the connector unit is mounted in a predetermined mounting position on the connecting nozzle of the external container.

10. The connector unit according to claim 9, wherein the release device is a reed contact, a capacitive sensor or a light barrier.

11. A system comprising a connector unit according to claim 1 and an external container.

12. A blood treatment machine comprising at least one connector unit according to claim 1, wherein the machine-side line is fluidly connected to the receiving aperture of the blood treatment machine.

13. A blood treatment machine comprising a plurality of connector units according to claim 1, each connector unit being fluid-connected via its machine-side line to a respective predetermined connector of the blood treatment machine, wherein the respective attachment of each connector unit of the plurality of connector units is configured to be detachably mountable only to a connecting nozzle of a respective dedicated predetermined type of external container, with the type of container corresponding to a content of the container.

14. The blood treatment machine according to claim 13, wherein each of the connector units of the blood treatment machine includes a release device which releases fluid flow between the blood treatment machine and a respective external container only when the attachment of the connector unit is correctly mounted in a predetermined mounting position on the connecting nozzle of the respective external container.

15. The connector unit according to claim 1, wherein the machine-side line, the container-side line, and at least an interior portion of the attachment are disinfected when the connector unit is in the disinfecting configuration.

* * * * *